(12) United States Patent
Planker

(10) Patent No.: US 6,423,274 B2
(45) Date of Patent: Jul. 23, 2002

(54) APPARATUS FOR MUFFLING AND DEODORIZING A GAS STREAM

(75) Inventor: Timothy W. Planker, Cape Coral, FL (US)

(73) Assignee: Hinsilblon Laboratories, Cape Coral, FL (US)

(*) Notice: Subject to any disclaimer, the term of this patent is extended or adjusted under 35 U.S.C. 154(b) by 0 days.

(21) Appl. No.: 09/783,209

(22) Filed: Feb. 15, 2001

Related U.S. Application Data

(60) Provisional application No. 60/182,892, filed on Feb. 16, 2000.

(51) Int. Cl.[7] .................................................. A61L 9/00
(52) U.S. Cl. ........................ 422/123; 422/5; 422/305; 422/306; 239/8
(58) Field of Search .............................. 422/123, 5, 4, 422/305, 306; 239/8, 311, 317

(56) References Cited

U.S. PATENT DOCUMENTS 2,731,167 A * 1/1956 Moore ............................ 220/4
5,766,547 A * 6/1998 Kay et al. ........................ 422/5
5,871,562 A * 2/1999 Culoso ............................ 95/26
6,142,383 A * 11/2000 Planker ............................ 239/8

* cited by examiner

Primary Examiner—Robert J. Warden, Sr.
Assistant Examiner—Sean E. Conley
(74) Attorney, Agent, or Firm—Arent Fox Kintner Plotkin & Kahn

(57) ABSTRACT

An apparatus for use with a sewage pumper truck to muffle and deodorize an air stream generated by filling of a tank of the truck though action of a vacuum pump on the exhaust of the tank to evacuate the tank and suck waste material into the tank. A reservoir contains a deodorizing liquid having a liquid surface and has a reservoir inlet positioned above the liquid surface and connectible to the outlet of the vacuum pump, and a reservoir outlet. An exhaust stack is connected to the outlet of the reservoir. Outside air heated by ordinary action of the vacuum pump pulling through the tank, is passed through the reservoir over the liquid surface of the deodorizing liquid, evaporates a sufficient amount of the liquid to achieve the desired effect, and then leaves the reservoir and is blown out the exhaust pipe containing the evaporated liquid.

8 Claims, 2 Drawing Sheets

FRONT VIEW

APPARATUS FOR MUFFLING AND DEODORIZING A GAS STREAM

This application claims priority of U.S. Provisional Patent application Ser. No. 60/182,892, filed on Feb. 16, 2000, the contents of which are hereby incorporated by reference in their entirety.

The present invention relates to an apparatus for use with a sewage pumper truck to muffle and deodorize the air stream generated by filling of the tank of the truck.

Pumper trucks have been in use for years where a septic tank or other waste facility periodically needs emptying. The tank of the truck is connected to the facility by hose and a vacuum pump or large scale blower inlet is connected to the exhaust of the tank. Turning on the vacuum pump exhausts the air from the tank to suck the contents of the facility into the tank.

Due to the nature of the contents, an odor problem occurs from the output of the air stream from the vacuum pump.

SUMMARY OF THE INVENTION

The present invention is an apparatus using direct vaporization acts as a muffler for the output air stream of the vacuum pump and provides deodorizing by vaporizing a deodorizing liquid directly into the air stream. In addition to very effective deodorizing, this system has the added benefit of being available at a very low capital cost and is easily maintained.

The present apparatus is especially useful in that it does not require any sophisticated electrical controller. The system can be manufactured with readily available component parts from local supply houses. The equipment can be operated and maintained with a minimal effort and is readily retro-fitted.

BRIEF DESCRIPTION OF THE DRAWINGS

The above and other objects and the attendant advantages of the present invention will become readily apparent by reference to the following detailed description when considered in conjunction with the accompanying drawings wherein.

DESCRIPTION OF PREFERRED EMBODIMENT

Figure 1:
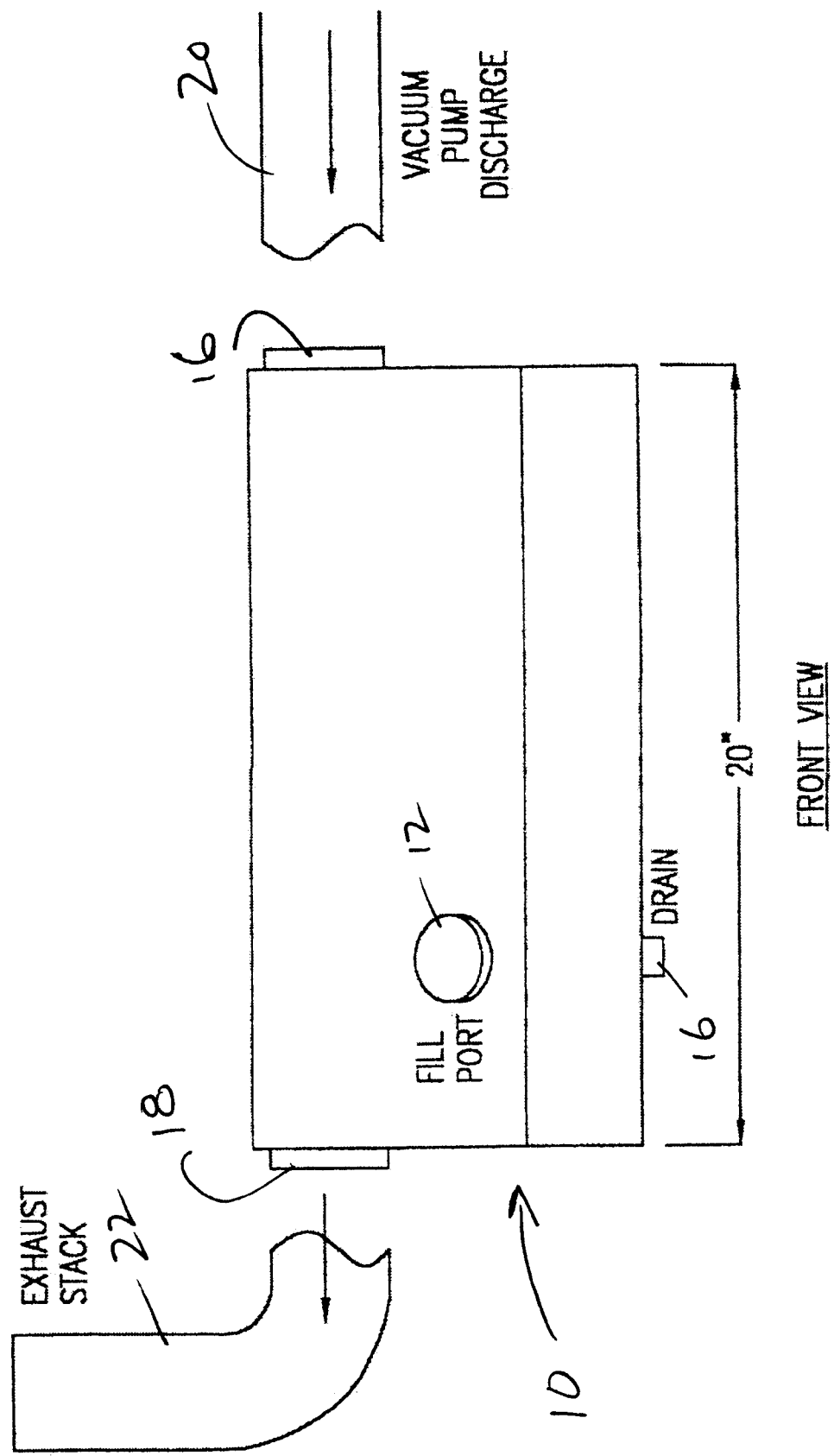
FIG. 1 is a front view of one embodiment of the present invention.
Figure 2:
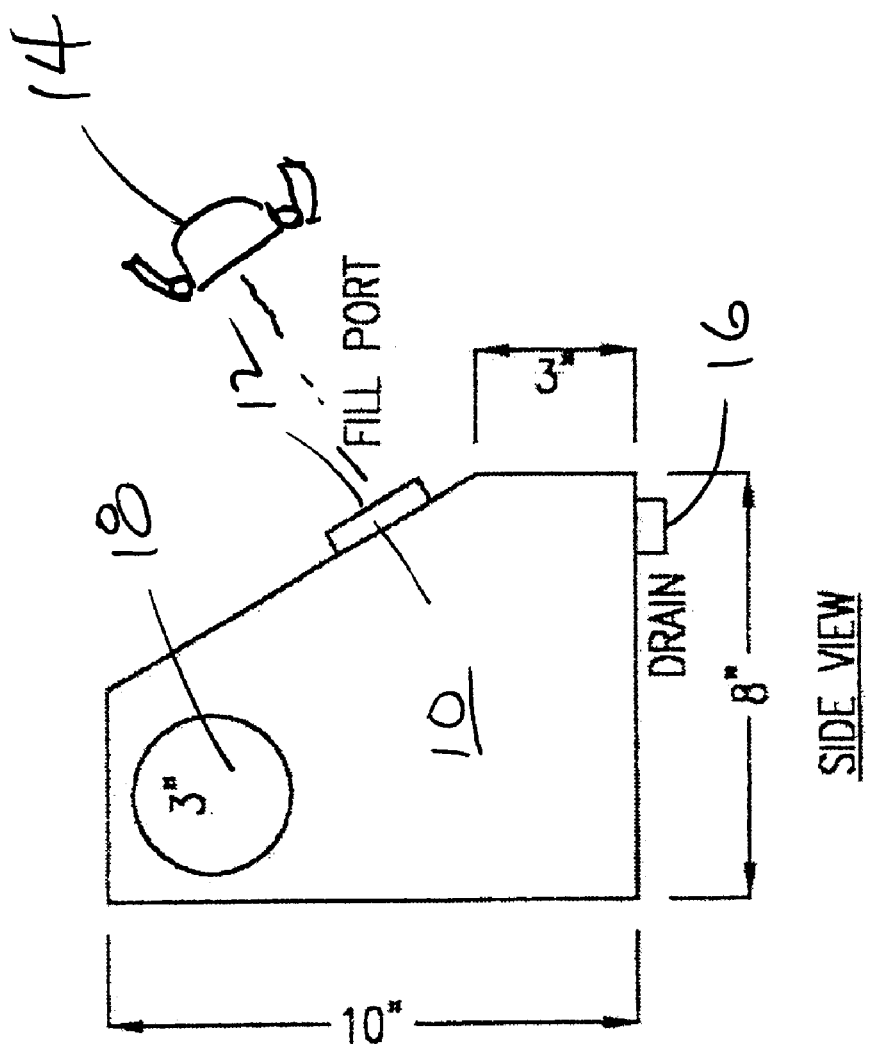
FIG. 2 is a side view of the same.

The equipment is essentially as shown in front view in FIG. 1 and in a side view in FIG. 2. In FIG. 1, the reservoir 10 is manually filled with the essential oil to be dispensed. The reservoir 10 is basically a rectangular box with four openings 12, 16, 18 and 20. In one model, the reservoir is made of welded aluminum and has a 7 ½ gallon capacity. One of the openings 12 is the fill port which when in use is closed by a cam lever type port cap 14. The other two 16, 18 have pipes 20, 22 connected to the vacuum pump and an exhaust stack, respectively. The vacuum pump (not shown) while pulling air through the tank of the pumper truck acts in a similar manner to a regenerative air blower.

The vacuum pump, reservoir, and extending exhaust stack or pipe can be easily mounted as a single unit on the pumper truck.

The outside air heated by the ordinary action of the vacuum pump pulling through the tank, is passed through the reservoir over the surface of a deodorizing liquid which has been poured in there. There is not believed to be any bubbling action and it is believed that the simple passage of the heated air over the liquid evaporates a sufficient amount of the liquid to achieve the desired effect. The heated air containing the liquid then leaves the reservoir and is blown out the exhaust pipe. To use the system, the truck is moved to the desired location, the hose is appropriately positioned, the deodorizing liquid is poured into the reservoir, the fill port is closed and capped, and the vacuum pump is started. The reservoir also appears to act as a muffler for the noise of the air stream.

As a deodorizing liquid, any commercial available deodorizing liquid can be used. One example would be Chloroxe®, a chlorine containing bleach.

It is readily apparent that the above-described has the advantage of wide commercial utility. It should be understood that the specific form of the invention hereinabove described is intended to be representative only, as certain modifications within the scope of these teachings will be apparent to those skilled in the art.

What is claimed is:

1. An apparatus for use with a sewage pumper truck to muffle and deodorize an air stream, the air stream being generated by filling of a tank of the truck by connecting an inlet of a vacuum pump to the exhaust of the tank to evacuate the tank and suck waste material into the tank, the air stream exiting an outlet of the vacuum pump, said apparatus comprising a reservoir for containing a deodorizing liquid having a liquid surface, said reservoir having a reservoir inlet positioned above the liquid surface and connectible to the outlet of the vacuum pump, and a reservoir outlet; and an exhaust stack connected to said outlet of said reservoir; whereby outside air heated by ordinary action of the vacuum pump pulling through the tank, is passed through the reservoir over the liquid surface of the deodorizing liquid, evaporates a sufficient amount of the liquid to achieve the desired effect, and then leaves the reservoir and is blown out the exhaust pipe containing the evaporated liquid.

2. The apparatus as claimed in claim 1 further comprising a fill port in said reservoir above the liquid surface and a port cap closing said fill port.

3. The apparatus as claimed in claim 1 wherein said reservoir is a rectangular box.

4. The apparatus as claimed in claim 1 wherein said reservoir is a rectangular box, and further comprises a fill port above the liquid surface and said apparatus further includes a port cap closing said fill port.

5. The apparatus as claimed in claim 1 wherein said reservoir is made of aluminum.

6. The apparatus as claimed in claim 1 wherein said reservoir is a rectangular box made of aluminum, and further comprising a fill port in said reservoir above the liquid surface and a port cap closing said fill port.

7. The apparatus as claimed in claim 1 wherein said exhaust stack extends vertically.

8. The apparatus as claimed in claim 1 wherein said reservoir is a rectangular box made of aluminum, and further comprises a fill port above the liquid surface; said apparatus further including a port cap closing said fill port; and wherein said exhaust stack extends vertically.

* * * * *